United States Patent [19]

Okino et al.

[11] Patent Number: 4,700,007

[45] Date of Patent: Oct. 13, 1987

[54] PROCESS FOR PREPARING MACROCYCLIC KETONES

[75] Inventors: Hiroshi Okino; Seiichi Uchida; Keita Matsushita, all of Saitama, Japan

[73] Assignee: Nippon Mining Co., Ltd., Tokyo, Japan

[21] Appl. No.: 824,816

[22] Filed: Jan. 31, 1986

[51] Int. Cl.[4] .............................................. C07C 45/65
[52] U.S. Cl. ..................................... 568/347; 568/346
[58] Field of Search ............... 568/346, 347, 355, 375, 568/392

[56] References Cited

U.S. PATENT DOCUMENTS

| 2,529,825 | 11/1950 | Stoll | 568/347 |
| 2,656,390 | 10/1953 | Stoll | 568/347 |
| 3,228,268 | 1/1961 | Hansley | 568/355 |
| 3,786,099 | 1/1974 | Howell | 568/346 |

FOREIGN PATENT DOCUMENTS

| 56-83436 | 7/1981 | Japan | 568/355 |

OTHER PUBLICATIONS

Vao et al., Chem. Abst. vol. 94, #208417q (1981).
Oop et al., Org. Synthesis, 218 (1963).
*Journal of the Chemical Society,* No. 452, 1962, pp. 2348–2352, Dhekne et al.

Primary Examiner—James H. Reamer
Attorney, Agent, or Firm—Sughrue, Mion, Zinn, Macpeak & Seas

[57] ABSTRACT

An improvement in a process for preparing a macrocyclic ketone having from 12 to 18 carbon atoms which comprises intramolecular cyclization of a lower alcohol diester of a straight chain alkanedicarboxylic acid having from 12 to 18 carbon atoms by acyloin condensation and reduction of the resulting 2-hydroxycycloalkanone is disclosed. The improvement comprises conducting the acyloin condensation in a water-immiscible organic solvent having a boiling point of not lower than 40°C., subjecting the resulting organic solvent solution containing the 2-hydroxycycloalkanone to reduction, and conducting the reduction in the copresence of said organic solvent and water. The macrocyclic ketone can be prepared at high efficiency.

12 Claims, No Drawings

PROCESS FOR PREPARING MACROCYCLIC KETONES

FIELD OF THE INVENTION

This invention relates to a process for preparing macrocyclic ketones and, more particularly, to an improved process for preparing macrocyclic ketones from lower alcohol esters of straight chain alkanedicarboxylic acids with high effeciency.

BACKGROUND OF THE INVENTION

Macrocyclic ketones represented by the following formula (I) have a musk aroma and are useful as perfumes or bases for perfumes:

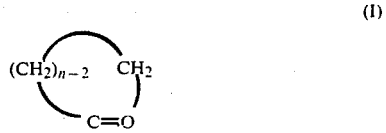

wherein n is an integer of from 12 to 18.

It is known that these macrocyclic ketones can be prepared by the following reaction scheme as described in Helv. Chem. Acta., 30, 1741 (1947) and Arther C. Cope et al., Organic Synthetis, 218 (1963):

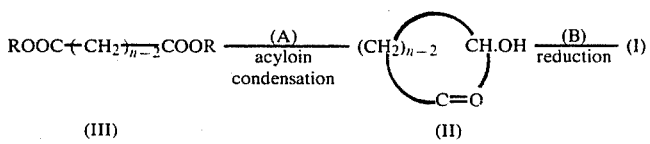

wherein n is as defined above; and R represents an alkyl group having from 1 to 4 carbon atoms.

According to this known process, the acyloin condensation (reaction A) is carried out in a sodium-aromatic hydrocarbon solvent system. After the reaction, an alkanol is added to the reaction mixture to convert unreacted sodium to a sodium alkoxide. The mixture is then neutralized with dilute sulfuric acid, and the aqueous phase is separated. The aromatic hydrocarbon solvent solution is washed successively with a sodium carbonate aqueous solution and water, dried and distilled under reduced pressure to isolate the compound represented by the formula (II). The resulting compound (II) is then reduced (reaction B) with zinc-hydrochloric acid in a glacial acetic acid solvent to thereby obtain the compound (I).

Since the above-described known process employs different solvents between reaction A (acyloin condensation) and reaction B (reduction), the process inevitably involves the isolation of the acyloin condensation product, which makes the process complicated and reduces the production efficiency. Moreover, use of glacial acetic acid in reaction B allows for a conversion rate near 100% but also tends to cause an excessive reduction to co-produce a large amount of cycloalkanes, resulting in low selectivity to macrocyclic ketones. As a result, the resulting macrocyclic ketones have reduced purity, which will be a bar to final use as perfumes and the like. Further, in the above-described process, the isolation of the resulting macrocyclic ketones after reduction is troublesome. For example, in the above-cited process, the macrocyclic ketones should be extracted with organic solvents that are incompatible with water, e.g., diethyl ether, and after washing the extract with water to remove water-soluble inorganic materials, recovered from the extract by distillation.

SUMMARY OF THE INVENTION

Accordingly, an object of this invention is to provide a process for preparing a macrocyclic ketone in which the acyloin condensation and the subsequent reduction can be carried out in the same solvent system so that the acyloin condensation product may be subjected to reduction without isolation.

Another object of this invention is to provide a process for preparing a macrocyclic ketone which can inhibit formation of by-products due to an excessive progress of reduction thereby providing ease in recovery of the product, thus realizing efficient production of macrocyclic ketones.

The present invention relates to an improvement in a process for preparing a macrocyclic ketone comprising intramolecular cyclization of a lower alcohol diester of a straight chain alkanedicarboxylic acid having from 12 to 18 carbon atoms by acyloin condensation to form a 2-hydroxycycloalkanone and reduction of the resulting 2-hydroxycycloalkanone, said improvement comprising conducting the acyloin condensation in a water-immiscible organic solvent having a boiling point of 60° C. or higher and conducting the reduction in the same organic solvent.

The present invention further relates to an improvement in a process for preparing a macrocyclic ketone comprising intramolecular cyclization of a lower alcohol diester of a straight chain alkanedicarboxylic acid having from 12 to 18 carbon atoms by acyloin condensation to form a 2-hydroxycycloalkanone and reduction of the resulting 2-hydroxycycloalkanone, said improvement comprising conducting the reduction with a metallic zinc power and hydrogen chloride in the copresnece of water and a water-immiscible organic solvent having a boiling point of 60° C. or higher and water.

DETAILED DESCRIPTION OF THE INVENTION

The diester represented by the formula (III) which can be used as a starting compound of the present invention can easily be obtained by reacting a straight chain alkanedicarboxylic acid having from 12 to 18 carbon atoms with a lower alcohol having from 1 to 4 carbon atoms in a known manner.

The acyloin condensation (A) can be effected in a dispersion of a metallic sodium power in a water-immiscible organic solvent having a boiling point of 60° C. or higher.

Specific examples of the organic solvent which can be used in the present invention include cyclohexane, toluence, aromatic hydrocarbon solvent, n-hexane, n-heptane, n-octane, 2-methylpentane, 2-methylhexane, isooctane, methyl ethyl ketone, ethyl butyl ketone, ethyl butyl ether, and mixtures of two or more thereof.

Any of the above-recited organic solvents can also be employed in the reduction (B). Solvents having a boiling point lower than 40° C. are not favorable since the reduction (B) is performed under the reaction condition with higher reaction rate, i.e., at a temperature of 40° C. or higher, and preferably from 60° C. to 120° C. The upper limit of the boiling point of the solvents is not particularly restricted, but is usually about 140° C. Solvents which are water-miscible are also unfavorable because the reduction is conducted in an aqueous dispersion system. Moreover, the reduction is sometimes carried out while azeotropically removing water for control of the water content of the reaction mixture and, therefore, solvents capable of forming azeotropic mixtures with water are preferred. Moreover, the use of water-immiscible solvents has such an advantage that water-soluble inorganic materials can be readily removed from the reaction mixture by washing with an aqueous solution. In this sense, cyclohexane and toluene are particularly preferred as the solvent.

The acyloin condensation can be achieved under high dilution conditions in favor of intramolecular cyclization. After completion of the reaction, the reaction mixture containing the thus produced 2-hydroxycloalkanone is filtered or centrifuged to separate any unreacted metallic sodium. Complete removal of fine sodium powders may be ensured by washing with a small amount of methanol, water, or dilute hydrochloric acid, but this procedure is not essential.

Since the acyloin condensation is conducted in a highly diluted solution in order to avoid intermolecular reaction of the starting diester, it is preferable to remove a part of the solvent used by distillation or a like method prior to reduction.

The concentrated reaction mixture is then subjected to reduction as it is. Reduction can be carried out in a dispersion of a powder of a metal selected from zinc, tin, and aluminum, and preferably zinc. Hydrogen chloride used as an acid is slowly supplied to the system as an aqueous solution having 3 or more normality, and preferably 6 or more normality, or as hydrogen chloride gas.

Solvents to be used in the reduction are the same as employed in the preceding acyloin condensation, i.e., water-immiscible organic solvents having a boiling point of from 40° C. to about 140° C. Cyclohexane and toluene are particularly preferred. The reduction is performed under the reaction condition with higher reaction rate, i.e., at a temperature ranging from 40° C. to 140° C., preferably from 60° C. to 120° C., and more preferably from 70° C. to 100° C. However, in a low temperature region as from 40° C. to 60° C., the reaction rate is low and, therefore, the reaction is preferably performed at 60° C. or higher and most preferably at from 70° C. to 100° C. Therefore, a solvent having too a low boiling point makes temperature control difficult. On the other hand, solvents having too a high boiling point are economically unfavorable because they require large heat in the recovery operation thereof and are rather difficult to purify for reuse.

The reduction is carried out in the copresence of water in an amount of from 3 to 100 parts by volume, preferably from 5 to 50 parts by volume, and more preferably from 7 to 30 parts by volume, per 100 parts by volume of the organic solvent. This is the reason for specifying that the organic solvent be water-immiscible.

Presence of water in the system within the above-recited range heightens the rate of reduction, while excessive water decreases the rate of reduction.

Water is introduced into the system either independently or as a solvent for hydrogen chloride, i.e., in the form of hydrochloric acid. In the latter case, where the water content of the system gruadually increases in the course of addition of hydrochloric acid, the water content can be controlled by driving a part or the whole of azeotropically distilled water out of the system during the reaction.

In the cases where an organic solvent which does not form an azeotrope is used, where an azeotrope-forming solvent used has a higher azeotropic point than the reaction temperature, or where the reaction apparatus used is not equipped with a means for recovery of an azeotrope; control of water content can sufficiently be achieved by adding from 3 to 30 parts by volume of water per 100 parts by volume of the organic solvent and/or an appropriate amount of a hydrochloric acid solution to the system either before or immediately after the start of the reaction and, thereafter, feeding hydrogen chloride gas and/or concentrated hydrochloric acid to the system to maintain the water content of the system in the preferable range.

In carrying out the reduction reaction, the starting reaction mixture as obtained by the aforesaid acyloin condensation is adjusted so as to contain from 1 to 60% by weight of the acyloin condensation product, i.e., a 2-hydroxycycloalkanone, based on the total amount of the starting solution, and a reducing metallic powder, e.g., zinc, is dispersed therein. The amount of the metallic powder to be added is preferably from 1.2 to 10 moles per mole of the 2-hydroxycycloalkanone. Concentrated hydrochloric acid or hydrogen chloride gas is portionwise added to the resulting dispersion in an amount of from 1.5 to 5 moles per mole of the reducing metal while maintaining the dispersion at a temperature of 40° C. or higher, preferably from 60° C. to 120° C., and more preferably from 70° C. to 100° C., to thereby effect reduction.

After completion of the reduction reaction, the desired macrocyclic ketone can be recovered from the reaction mixture by allowing the mixture to stand for phase separation and removing the solvent from the organic phase by distillation.

The thus recovered reaction product can be purified by known purification techniques, such as distillation under reduced pressure, formation of an adduct, liquid chromatography, recrystallization, and the like, to obtain a macrocyclic ketone of high purity.

The present invention will now be illustrated in greater detail with reference to the following examples and comparative examples, but it should be understood that the present invention is not construced to be limited thereto. In these examples, all ratios, percents, etc., are by weight and weight is expressed as pure compound unless otherwise indicated.

EXAMPLE 1

A 10-liter volume flask equipped with a bulk-type reflux condenser, a dropping funnel, and a stirrer was charged with 4 liters of toluene and 40 g metallic sodium powder, and the mixture was kept at 105° C. in a nitrogen stream. A solution of 100 g of diethyl n-hexadecanedioate in 250 ml of toluene was added dropwise thereto over a period of 15 hours. After the dropwise addition, the reaction mixture was maintained at 105° C.

for 1 hour, followed by allowing the mixture to cool. After a small amount of 2N hydrochloric acid was added thereto, the reaction mixture was filtered. To the filtrate was added 200 ml of water. After stirring, the mixture was left to stand, and the aqueous phase was separated. This step was repeated twice. The organic phase was distilled under reduced pressure in a nitrogen stream to remove the toluene, whereby 400 ml of a concentrated solution containing the acyloin condensation product was obtained.

To the resulting concentrated solution was added 80 g of a zinc powder, and 200 ml of 12N hydrochloric acid was added dropwide thereto over 1.5 hours while thoroughly stirring at about 98° C. During the reaction, an azeotropic mixture was refluxed below 100° C., and the whole amount of the water in the azeotropic mixture was removed out of the system, with the organic solvent in the azeotropic mixture being recycled to the system. After completion of the reaction, the reaction mixture was allowed to stand, and the aqueous phase was separated. The organic phase was filtered, washed successively with a 10% aqueous solution of sodium carbonate and water, and dehydrated and dried over 10 g of anhydrous sodium sulfate. After removal of the toluene by evaporation, the residue was distilled under reduced pressure of not more than 2 Torr to obtain 42.3 g (purity: 90.5%) of cyclohexadecanone, which corresponded to 55% of a theoretical value based on the starting compound.

EXAMPLE 2

The same procedures as described in Example 1 were repeated except that a solution of 110 g of dimethyl n-pentadecanedioate in 250 ml of cyclohexane was used as a starting material. There was obtained 51 g of cyclopentadecanone, which corresponded to 62.1% of a theoretical value based on the starting compound.

COMPARATIVE EXAMPLE 1

In a 10 liter-volume Herz flask was placed 4 liters of dehydrated xylene, and 39.8 g of metallic sodium was added thereto. The mixture was kept at 105° C. in a nitrogen streatm. A solution of 110 g of dimethyl n-pentadecanedioate in 250 ml of xylene was added dropwise to the mixture over a period of 15 hours. After completion of the dropwise addition, the mixture was allowed to stand at 105° C. for 1 hour, followed by cooling to 80° C. To the cooled mixture was slowly added dropwise 200 ml of methanol. After ice-cooling, the reaction mixture was neutralized with 150 ml of glacial acetic acid, and the aqueous layer was separated. The organic layer was distilled under reduced pressure to obtain 65.0 g of the acyloin condensation product (b.p.: 152°-166° C./0.33-0.95 mmHg). The purity of the thus isolated 2-hydroxycyclopentadecanone was 89.5%.

In 100 ml of acetic acid was dispersed 45.5 g of a zinc powder, and 65.0 g of the above obtained product was dissolved in the resulting dispersion. The mixture was heated at 75° to 80° C., and 50 ml of 12N hydrochloric acid was added dropwise thereto over a period of 5 to 10 minutes at that temperature, followed by stirring for 20 to 25 minutes. The above-described dropwise addition followed by stirring was repeated 3 times to complete the reaction. The unreacted zinc powder was separated by filtration. To the filtrate was added 500 ml of a saturated aqueous solution of sodium chloride, and the mixture was extracted twice each with 200 ml of diethyl ether. The extract was washed successively with 200 ml of a 10% sodium carbonate aqueous solution and 200 ml of a saturated sodium chloride aqueous solution, dried over about 10 g of anhydrous magnesium sulfate, and filtered. Almost all of the diethyl ether was distilled away by evaporation, and the residue was distilled under reduced pressure to obtain 37.4 g of cyclopentadecanone, which corresponded to 45.5% of a theoretical value based on the starting dimethyl pentadecanedioate.

EXAMPLES 3 TO 10

Thirty grams each of 2-hydroxycyclopentadecanone, 2-hydroxycyclotridecanone, 2-acetoxycyclopentadecanone, 2-acetoxycyclotridecanone, and 2-hydroxycyclohexadecanone obtained through acyloin condensation was dissolved in 200 ml of an organic solvent shown in Table 1. The resulting solution was placed in a reaction apparatus equipped with a reflux condenser having a water trap, a stirrer, and a dropping funnel, and 40 g of a zinc powder was dispersed therein. The mixture was allowed to react under reflux by adding 150 ml of 12N hydrochloric acid dropwise over a period of 1.5 hours. During the reaction, the aqueous layer in the trap was intermittently withdrawn in the case of using toluene, xylene, or cyclohexane as an organic solvent. In the case of using methyl ethyl ketone, the whole amount of the liquid reserved in the trap (about 90 ml) was intermittently withdrawn.

After completion of the reaction, the reaction mixture was washed successively with a 10% sodium carbonate aqueous solution and water, dried over about 10 g of anhydrous magnesium sulfate, and filtered. Almost all of the solvent was removed by evaporation, and the residue was subjected to distillation under reduced pressure of not more than 2 Torr to recover the respective cycloalkanones. The results obtained are shown in Table 1.

EXAMPLE 11

In order to examine the influence of reaction time on yields, the same procedures as described for Example 3 were repeated except that after the dropwise addition of 150 ml of 12N hydrochloric acid, an additional 100 ml of 12N hydrochloric acid was further added dropwise over 1 hour while continuing stirring and heating. The results obtained are shown in Table 1.

COMPARATIVE EXAMPLES 2 TO 4

In 100 ml of acetic acid was dispersed 21 g of a zinc powder, and 30 g of each of 2-hydroxycyclopentadecanone, 2-hydroxycyclotridecanone, and 2-hydroxycyclohexadecanone obtained through acyloin condensation was dissolved in the dispersion. The mixture was heated to 75° to 80° C., and 50 ml of 12N hydrochloric acid was added dropwise thereto over a period of 5 to 10 minutes, followed by stirring for 20 to 25 minutes while maintaining the mixture at the same temperature. The procedure of dropwise addition followed by stirring was repeated 3 times to complete the reaction.

The unreacted zinc powder was separated by filtration, and to the filtrate was added 500 ml of a saturated aqueous solution of sodium chloride. The mixture was extracted twice each with 200 ml of diethyl ether. The extract was washed successively with 200 ml of a 10% sodium carbonate aqueous solution and 200 ml of a saturated sodium chloride aqueous solution, dried over about 10 g of anhydrous magnesium sulfate, and filtered. Almost all of the diethyl ether was distilled off by an evaporator, and the residue was distilled under reduced pressure of not more than 2 Torr to thereby recover the respective cycloalkanones. The results obtained are shown in Table 1.

TABLE 1

| Example No. | Starting Compound | Organic Solvent | Yield (g) | Yield Based on Theoretical Value (%) |
|---|---|---|---|---|
| Example 3 | 2-hydroxycyclopentadecanone | Cyclohexane | 22.2 | 79.3 |
| Example 4 | 2-hydroxycyclopentadecanone | toluene | 22.1 | 78.9 |
| Example 5 | 2-hydroxycyclopentadecanone | xylene | 21.0 | 75.0 |
| Example 6 | 2-hydroxycyclopentadecanone | methyl ethyl ketone | 20.8 | 74.3 |
| Example 7 | 2-acetoxycyclopentadecanone | cyclohexane | 18.6 | 78.1 |
| Example 8 | 2-hydroxycyclotricecanone | cyclohexane | 22.8 | 82.3 |
| Example 9 | 2-acetoxycyclotridecanone | cyclohexane | 18.5 | 80.0 |
| Example 10 | 2-hydroxycyclohexadecanone | cyclohexane | 23.2 | 82.5 |
| Example 11 | 2-hydroxycyclopentadecanone | cyclohexane | 21.5 | 76.8 |
| Comparative Example 2 | 2-hydroxycyclopentadecanone | acetic acid | 19.0 | 67.9 |
| Comparative Example 3 | 2-hydroxycyclotridecanone | acetic acid | 20.5 | 73.9 |
| Comparative Example 4 | 2-hydroxycyclohexadecanone | acetic acid | 20.2 | 71.8 |

The results of Table 1 above demonstrate that the process according to the present invention increases the yield as compared with the conventional process which employs acetic acid as a solvent for the reduction reaction.

Further, it can be seen by comparing the results of Example 3 and Example 11 that extension of the reaction period does not make any significant difference in yield.

EXAMPLES 12 AND 13 AND COMPARATIVE EXAMPLES 5 AND 6

A cyclohexane solution containing 30 g of 2-hydroxycyclopentadecanone prepared by acyloin condensation was placed in a flask equipped with a reflux condenser having a water trap. Twenty grams of a zinc powder was added to the solution, and 150 ml of 12N hydrochloric acid was added dropwise thereto over 1.5 hours to effect reduction. During the reaction, the temperature was maintained at an azeotropic point for cyclohexane and water, and a part of the azeotropically distilled water was driven out of the system to control the proportion of water to cyclohexane in the system as shown in Table 2. The composition of the reaction product in the reaction mixture was analyzed by gas-liquid chromatography, and the results obtained are shown in Table 2.

For comparison, the same procedures as described above were repeated except using water-miscible acetic acid in place of cyclohexane. The results are also shown in Table 2 below.

TABLE 2

|  | Example 12 | Example 13 | Comp. Ex. 5 | Comp. Ex. 6 |
|---|---|---|---|---|
| Organic Solvent: |  |  |  |  |
| Cyclohexane (ml) | 100 | 100 | 30 | — |
| Acetic Acid (ml) | — | — | — | 100 |
| Water Content of System (ml) | 53 | 25 | 100 | 40 |
| Solvent: Water (by vol.) | 100:53 | 100:25 | 100:125 | 100:40 |
| Yield*: |  |  |  |  |
| Cyclopentadecanone (%) | 81.0 | 79.5 | 70.9 | 58.0 |
| By-products (cyclopentadecane, etc.) (%) | 10.4 | 7.7 | 16.2 | 30.1 |
| Conversion (%) | 100 | 100 | 100 | 100 |

Note:
*The yields were base on the starting 2-hydroxcyclopentadecanone.

It is apparent from Table 2 above that use of acetic acid which is miscible with water results in formation of large amounts of by-products, e.g., cyclopentadecane, etc., and reduction of yield of the desired cyclopentadecanone. Further, it can also be seen that a large water content with respect to the organic solvent as in Comparative Example 5 reduces the yield.

EXAMPLE 14

To 37 ml of a toluene solution containing 3.5 g of 2-hydroxypentadecanone prepared by acyloin condensation were added 5.7 g of a zinc powder and 5 ml of water, and the mixture was maintained at 75° C. In the initial stage of the reaction, 5 ml of 12N hydrochloric acid was slowly added with stirring, and then 3 liters of hydrogen chloride gas was slowly but continuously fed to the system over a period of time of 1.5 hours while stirring. Refluxing was not conducted during the reaction and, therefore, the volumeric proportion of toluene to water was 100/14 throughout the reaction. There was obtained the desired cyclopentadecanone in a yield of 81.0% and a smaller yield of by-products, e.g., cyclopentadecane, etc. (7.5%).

While the invention has been described in detail and with reference to specific embodiments thereof, it will be apparent to one skilled in the art that various changes and modifications can be made therein without departing from the spirit and scope thereof.

What is claimed is:

1. In a process for preparing a macrocyclic ketone having from 12 to 18 carbon atoms from a lower alcohol diester of a straight chain alkanedicarboxylic acid having from 12 to 18 carbon atoms, an improvement comprising (a) subjecting said diester to acyloin condensation in a water-immiscible organic solvent having a boiling point of not lower than 40° C. to obtain a reaction mixture containing a 2-hydroxycycloalkanone as a condensation reaction product and then (b), without isolating said condensation reaction product from said reaction mixture, reducing said 2-hydroxycycloalkanone while bringing into contact with a metallic powder selected from the group consisting of zinc, tin and aluminum and hydrogen chloride in the copresence of from 3 to 100 parts by volume, based on 100 parts by volume of said organic solvent, of water, followed by recovering said macrocyclic ketone from the reaction mixture, wherein said water-immiscible organic solvent is one or more members selected from the group consisting of cyclohexane, toluene, xylene, n-hexane, n-heptane, n-octane, 2-methylpentane, 2-methylhexane, isooctane, methyl ethyl ketone, ethyl butyl ketone, and ethyl butyl ether.

2. A process as in claim 1, wherein a part of said organic solvent used in the acyloin condensation is removed prior to reduction.

3. A process as in claim 1, wherein said water-immiscible organic solvent is capable of forming an azeotropic mixture with water.

4. A process as in claim 1, wherein said water-immiscible organic solvent is cyclohexane or toluene.

5. A process as in claim 1, wherein the 2-hydroxycycloalkanone is acetylated prior to reduction.

6. A process as in claim 1, wherein said water is present in an amount of from 5 to 50 parts by volume per 100 parts by volume of said organic solvent.

7. A process as in claim 6, wherein said water is present in an amount of from 7 to 30 parts by volume per 100 parts by volume of said organic solvent.

8. A process as in claim 1, wherein said hydrogen chloride is an aqueous solution having at least 3 normality and/or hydrogen chloride gas.

9. A process as in claim 8, wherein said hydrogen chloride is an aqueous solution having at least 6 normality and/or hydrogen chloride gas.

10. A process as in claim 1, wherein the reduction is carried out under reflux to form an azeotropic mixture of said organic solvent and water and a part or the whole of the azeotropically distilled water is removed from the system.

11. A process as in claim 10, wherein said organic solvent is capable of forming an azeotropic mixture with water at a temperature of from 40° C. to about 140° C.

12. A process as in claim 1, wherein from 3 to 30 parts by volume of water per 100 parts by volume of said organic solvent and/or hydrochloric acid having at least 3 normality are or is added to the reduction system before or immediately after the start of the reduction, and hydrogen chloride gas is then added to the system.

* * * * *